US008055331B2

(12) United States Patent
Satin et al.

(10) Patent No.: US 8,055,331 B2
(45) Date of Patent: Nov. 8, 2011

(54) METHOD AND APPARATUS FOR SEQUENCED EXTRACTION FROM ELECTROCARDIOGRAMIC WAVEFORMS

(75) Inventors: Scott L. Satin, Washington, DC (US); Robert G. Cochran, New Market, MD (US); Nirmal R. Patel, Croydon, PA (US)

(73) Assignee: Cardiocore Lab, Inc., Bethesda, MD (US)

( * ) Notice: Subject to any disclaimer, the term of this patent is extended or adjusted under 35 U.S.C. 154(b) by 888 days.

(21) Appl. No.: 11/383,376

(22) Filed: May 15, 2006

(65) Prior Publication Data
US 2006/0264768 A1  Nov. 23, 2006

Related U.S. Application Data

(60) Provisional application No. 60/680,524, filed on May 13, 2005.

(51) Int. Cl.
*A61B 5/04* (2006.01)
(52) U.S. Cl. ......................................... 600/509; 600/513
(58) Field of Classification Search .................. 600/509, 600/513
See application file for complete search history.

(56) References Cited

U.S. PATENT DOCUMENTS

| 4,583,553 | A  | * | 4/1986  | Shah et al. ..................... 600/517 |
| 5,271,411 | A  | * | 12/1993 | Ripley et al. ................... 600/515 |
| 5,971,930 | A  | * | 10/1999 | Elghazzawi .................... 600/483 |
| 6,236,883 | B1 |   | 5/2001  | Ciaccio et al. |
| 6,405,076 | B1 | * | 6/2002  | Taylor et al. ................... 600/513 |
| 7,058,444 | B2 | * | 6/2006  | Logan et al. ................... 600/523 |
| 2002/0183640 | A1 |   | 12/2002 | Bjorling |
| 2003/0135097 | A1 | * | 7/2003  | Wiederhold et al. .......... 600/301 |
| 2004/0054294 | A1 | * | 3/2004  | Ramseth ........................ 600/509 |
| 2004/0054295 | A1 |   | 3/2004  | Ramseth |
| 2004/0230105 | A1 |   | 11/2004 | Geva et al. |
| 2005/0177050 | A1 | * | 8/2005  | Cohen ........................... 600/509 |
| 2005/0182334 | A1 | * | 8/2005  | Korzinov et al. .............. 600/509 |
| 2005/0222507 | A1 | * | 10/2005 | Logan et al. ................... 600/509 |
| 2005/0256413 | A1 | * | 11/2005 | Astrom et al. ................. 600/509 |
| 2005/0277992 | A1 | * | 12/2005 | Koh et al. ......................... 607/9 |
| 2006/0052833 | A1 | * | 3/2006  | Legay et al. ..................... 607/27 |
| 2006/0084881 | A1 | * | 4/2006  | Korzinov et al. .............. 600/509 |
| 2006/0189876 | A1 | * | 8/2006  | Couderc et al. ............... 600/516 |
| 2006/0270937 | A1 | * | 11/2006 | Koyrakh et al. ............... 600/509 |
| 2006/0281996 | A1 | * | 12/2006 | Kuo et al. ....................... 600/509 |

FOREIGN PATENT DOCUMENTS

WO    0167950 A1    9/2001

* cited by examiner

*Primary Examiner* — Niketa Patel
*Assistant Examiner* — Nicole F Lavert
(74) *Attorney, Agent, or Firm* — Sughrue Mion, PLLC

(57) ABSTRACT

A method for extracting segments from an electrocardiogram tracing is disclosed. The method selects an electrocardiogram tracing for segment extraction, and associates a dosing time or other time point with the electrocardiogram tracing to align an extraction template within the electrocardiogram tracing for segment extraction. The electrocardiogram tracing is scanned for artifacts and the electrocardiogram tracing is annotated if any artifacts are discovered. If there are any artifacts present in the segment designated for extraction by the extraction template, the extraction template is modified to avoid the artifacts. If the extraction template cannot be modified, the electrocardiogram tracing is annotated as unextractable. If artifacts are not present in the segment designated for extraction by the extraction template or the extraction template was successfully modified, the designated segment is extracted from the electrocardiogram tracing and written to a storage medium.

31 Claims, 11 Drawing Sheets

METHOD AND APPARATUS FOR SEQUENCED EXTRACTION FROM ELECTROCARDIOGRAMIC WAVEFORMS

CROSS-REFERENCES TO RELATED APPLICATIONS

This application claims priority from U.S. Provisional Application No. 60/680,524, filed on May 13, 2005 in the United States Patent and Trademark Office, the disclosure of which is incorporated herein in its entirety by reference.

BACKGROUND OF ILLUSTRATIVE EMBODIMENTS OF THE INVENTION

The heart is a pump comprised of muscle tissue that responds to electrical stimulation. A heartbeat is a precisely controlled event that relies on synchronization between the atrial and ventricular chambers to maximize pumping efficiency. The sinoatrial node, which is located in the right atrium of the heart, generates the electrical stimulus. In a healthy person, the sinoatrial node normally generates electrical stimulus signals at a 60-100 Hz rate, and the waves of myocardial excitation and contraction spread throughout the heart in well-defined manner. The electrical stimulus signals cause contractions in the heart's chambers, thereby pumping blood through the chambers. The left and right atria of the heart contract first and for a brief time, and then the left and right ventricles contract for a brief time. Normal heart rhythm is referred to as "sinus" rhythm, because it originates in the sinoatrial node (also referred to as the sinus node). The electrical stimulus signal output by the sinoatrial node is first sent to the left and right atria, then through the atrioventricular node and into the left and right ventricles.

An electrocardiogram (ECG) measures the heart's electrical activity. Electrodes are placed at specific locations on the body to capture a tracing of the heart's electrical activity. The electrical activity resulting from heart depolarization and heart repolarization is recorded by each lead. The ECG is a summation of the information recorded from each lead. The captured ECG reflects the direction of electrical current flow, and the magnitude of the muscle that is depolarized. Therefore, when the atria depolarize (and contract) the ECG tracing is smaller as compared to when the ventricles contract, since the atria are much smaller than the ventricles. Ventricle repolarization is in the same direction (positive) as ventricle depolarization. Although an ECG is positive during membrane depolarization and negative during repolarization, the direction with respect to ventricles is the same since ventricles depolarize from the inside to the outside (endocardium to epicardium), while repolarization occurs in the opposite direction.

Referring to FIG. 1, an ECG tracing is illustrated. The cardiac cycle begins with a P-wave, wherein the spontaneously firing cells in the sinoatrial node reach a threshold and generate action potentials. A wave of depolarization that spreads to the left and downward though left and right atria, which is labeled in FIG. 1 as the "P wave." The atria that were hyperpolarized suddenly become depolarized and the ECG records a positive deflection. When the left and right atria become depolarized, the ECG returns to zero. The electrical current passes through the atrioventricular node, causing a delay of about one-tenth of a second, and due to the small mass of the atrioventricular node, the ECG tracing does not record any electrical activity. When the atrioventricular node is depolarized, it triggers depolarization of the Purkinje fibers. The Purkinje fibers spread the electrical current throughout the left and right ventricles, thereby causing depolarization across each ventricle simultaneously. Since the tissue mass of the Purkinje fibers is small, the ECG tracing does not record any electrical activity. The passing of the electrical current through the atrioventricular node and the Purkinje fibers is labeled in FIG. 1 as the "PR segment."

The depolarization of the left and right ventricles is referred to as the "QRS complex" and FIG. 1 is labeled as such. The QRS complex is quite large since the left and right ventricle tissue is large in comparison to the sinoatrial node. The three peaks are indicative of the manner in which the electrical current spreads through the left and right ventricles, i.e., from inside to outside, and are indicative of the fact that the tissue mass of the left ventricle is greater than the tissue mass of the right ventricle. The complete depolarization of the left and right ventricles indicates that the QRS complex has terminated.

Referring to FIG. 2, the points of the QRS complex are labeled. As noted above, the QRS complex is indicative of the depolarization of the left and right ventricles. The ventricular depolarization begins at a left side of the intraventricular septum and the peak of this depolarization is shown by the "Q" peak of the QRS complex. The ventricular depolarization spreads from the endocardial surface of the left ventricle to the epicardial surface of the left ventricle, and is shown by the "R" peak of the QRS complex. The spread of the ventricular depolarization to the right ventricle is shown by the "S" peak of the QRS complex.

The segment labeled "T wave" indicates repolarization of the left and right ventricles. Although the left and right ventricles are repolarizing, the T wave is positive, since the heart repolarizes from outside to inside, the opposite direction of depolarization (inside to outside). The completion of the T wave signals the end of the cardiac cycle.

Referring to FIG. 3, the captured tracing of electrical activity is printed out on a paper tape or is presented on a display. Anomalies in an ECG are indicative of various heart-related conditions, such as ischemia, myocardial infarction, conduction disorder, electrolyte disturbance, pericarditis, valve disease or enlarged heart. Certain arrhythmias might occur only on an intermittent basis, or only if certain psychological or physical factors (i.e., stress, fatigue, etc.) are present. Since a typical ECG tracing is only a few minutes in length, arrhythmias of this type are difficult to capture. A more lengthy ECG tracing, referred to as a Holter monitor, will be used to capture any arrhythmias or other abnormal activity. The Holter monitor may record a heart's activity over a period of several days.

Referring to FIG. 1, one of the measured segments is referred to as the QT interval, and the QT interval indicates the duration of the electrical activity that controls contraction of the cells of the heart muscle. The QT interval represents the duration of ventricular depolarization and subsequent repolarization, beginning at the initiation of the Q wave of the QRS complex and ending where the T wave returns to isoelectric baseline. QT interval prolongation creates an electrophysiological environment that favors the development of cardiac arrhythmias, most clearly torsade de pointes, but possibly other ventricular arrhythmias as well. Long QT syndrome identifies a condition wherein there exists an abnormally long QT interval on the ECG tracing. The term "congenital long QT" refers to a long QT interval that is inherited. The inherited form occurs due to irregularities in particular heart cell proteins, and, of course, these protein irregularities are caused by abnormalities in the genes that produce those proteins. The term "acquired long QT" refers to a long QT interval that is brought about by drugs or anomalous levels of the salts within blood, e.g., potassium and magnesium.

Although a person might have an unremarkable QT interval under normal conditions, that person might develop a prolonged QT or suffer torsades de pointes (TdP) when taking certain medications. As shown in FIG. 4, TdP refers to the characteristic appearance of the electrocardiogram indicative of a rhythm abnormality, and typically occurs in the setting of a prolonged QT interval on the electrocardiogram. TdP is a polymorphic ventricular tachyarrhythmia that manifests on the ECG tracing as continuous twisting of the vector of the QRS complex around the isoelectric baseline. A feature of TdP is pronounced prolongation of the QT interval in the sinus beats preceding the arrhythmia. TdP can degenerate into life-threatening cardiac rhythms that can result in blackouts or sudden death. Measurement of the QT interval on the ECG tracing is still the main method of determining whether a person has long QT interval syndrome, whether inherited or acquired.

Non-antiarrhythmic drugs can have an undesirable side effect of causing delayed cardiac repolarization. Due to its relationship to heart rate, the QT interval is normalized into a heart rate independent "corrected" value known as the $QT_c$ interval, which represents the QT interval at a standardized heart rate (essentially the QT interval at a heart rate of 60 bpm). Several drugs that have caused TdP clearly increase both the absolute QT and the $QT_c$.

SUMMARY OF ILLUSTRATIVE EMBODIMENTS OF THE INVENTION

Illustrative, non-limiting embodiments of the present invention overcome various disadvantages. In addition, the present invention is not required to overcome these disadvantages, and an illustrative, non-limiting embodiment of the present invention may not overcome any disadvantages.

Illustrative, non-limiting embodiments of the present invention provide apparatuses and methods for automatically extracting a number of short segments of data from a single long ECG recording based on settings defined by a protocol associated with a medical study, and transmitting the data to a central location.

One aspect of an embodiment provides an extraction template that specifies times and amounts of data to extract relative to drug dosing time or time points specified in the study protocol. Different protocols may have different specific extraction templates which apply across all subjects and all days in the particular studies. As an example, an extraction template may be set to extract a few ten-second segments of an ECG, spaced apart by two to three minutes, every thirty to sixty minutes over the duration of the ECG. These values are merely examples, and the extraction template is completely configurable by the user.

Another aspect of an embodiment chooses ECG segments to extract in an intelligent manner. The presence of signal artifacts and other specified conditions in the ECG segments are checked, and, if present, those ECG segments are avoided. To avoid extracting corrupted data, the extraction template may be automatically adjusted by a limited amount to extract data close to the desired extraction times. Extracted ECG segments may be exported to separate data files.

A further aspect of an embodiment provides a remote mode which extracts sections of ECG data at the point of capture and transmits the extracted data to a central location at a higher priority. In the remote mode, artifact detection and avoidance may be suspended, and the extraction template may be widened to include segments of data on either side of the requested extraction times.

A further aspect of an embodiment provides a method of extracting ECG data segments that includes specifying the parameters of the configurable extraction template, specifying data files from which to extract data, intelligently extracting the data, and writing the extracted data segments to separate data files. The method may also include transmitting the data files to a central location.

Additional aspects and advantages of the embodiments will be set forth in part in the description that follows or may be learned by practice of the embodiments. The aspects and advantages of the embodiments may be realized and attained by means of the instrumentalities and combinations particularly pointed out in the appended claims.

BRIEF DESCRIPTION OF THE DRAWINGS

The above and other features and advantages will become more apparent by describing in detail exemplary embodiments. The accompanying drawings, which are incorporated in and constitute a part of this specification, illustrate the exemplary embodiments and, together with the description, serve to explain various aspects, advantages and principles. In the drawings.

Figure 1:
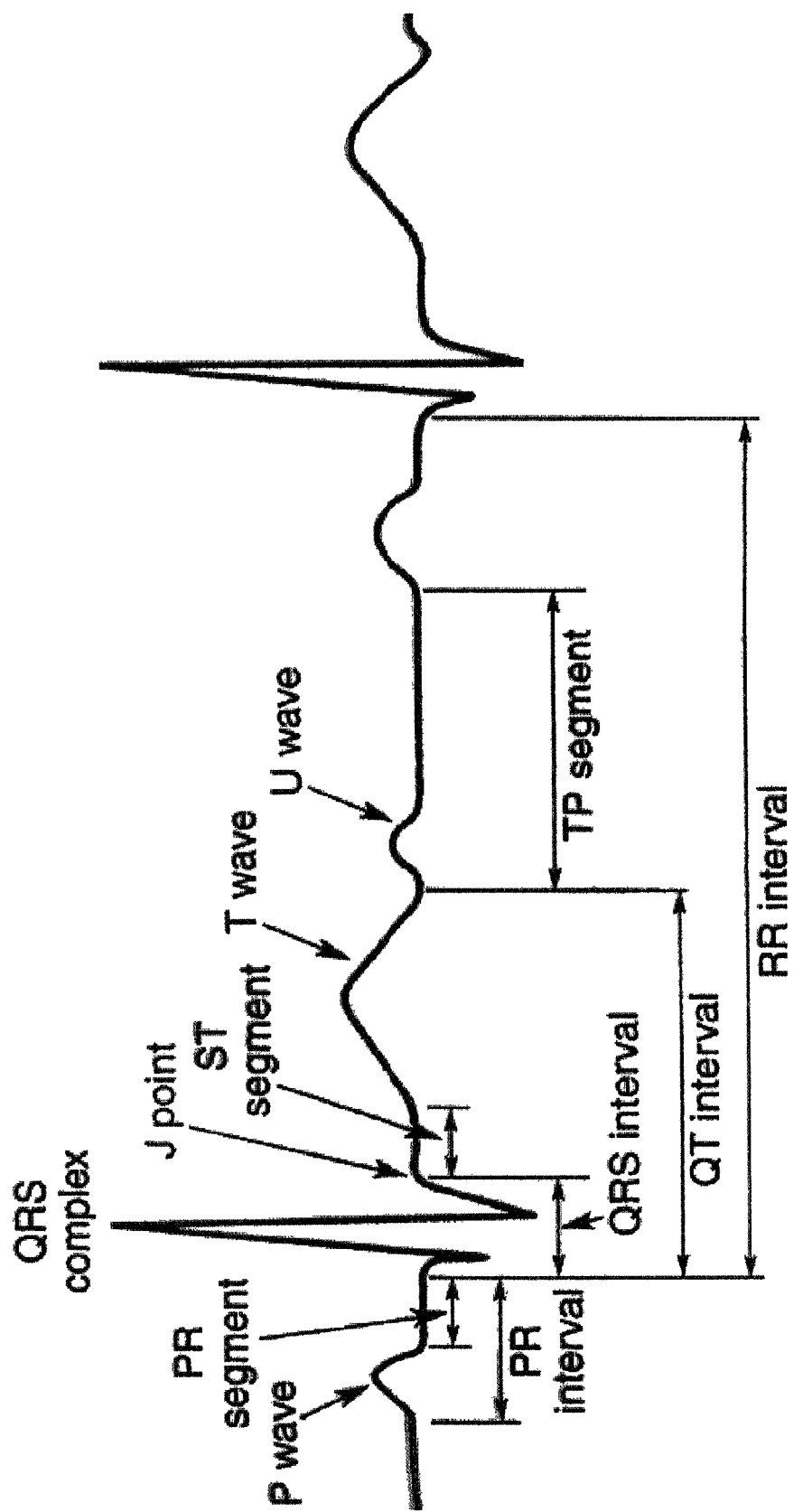
FIG. 1 is an illustration of an ECG tracing that identifies the various segments of an electrical profile of a normal heartbeat.
Figure 2:
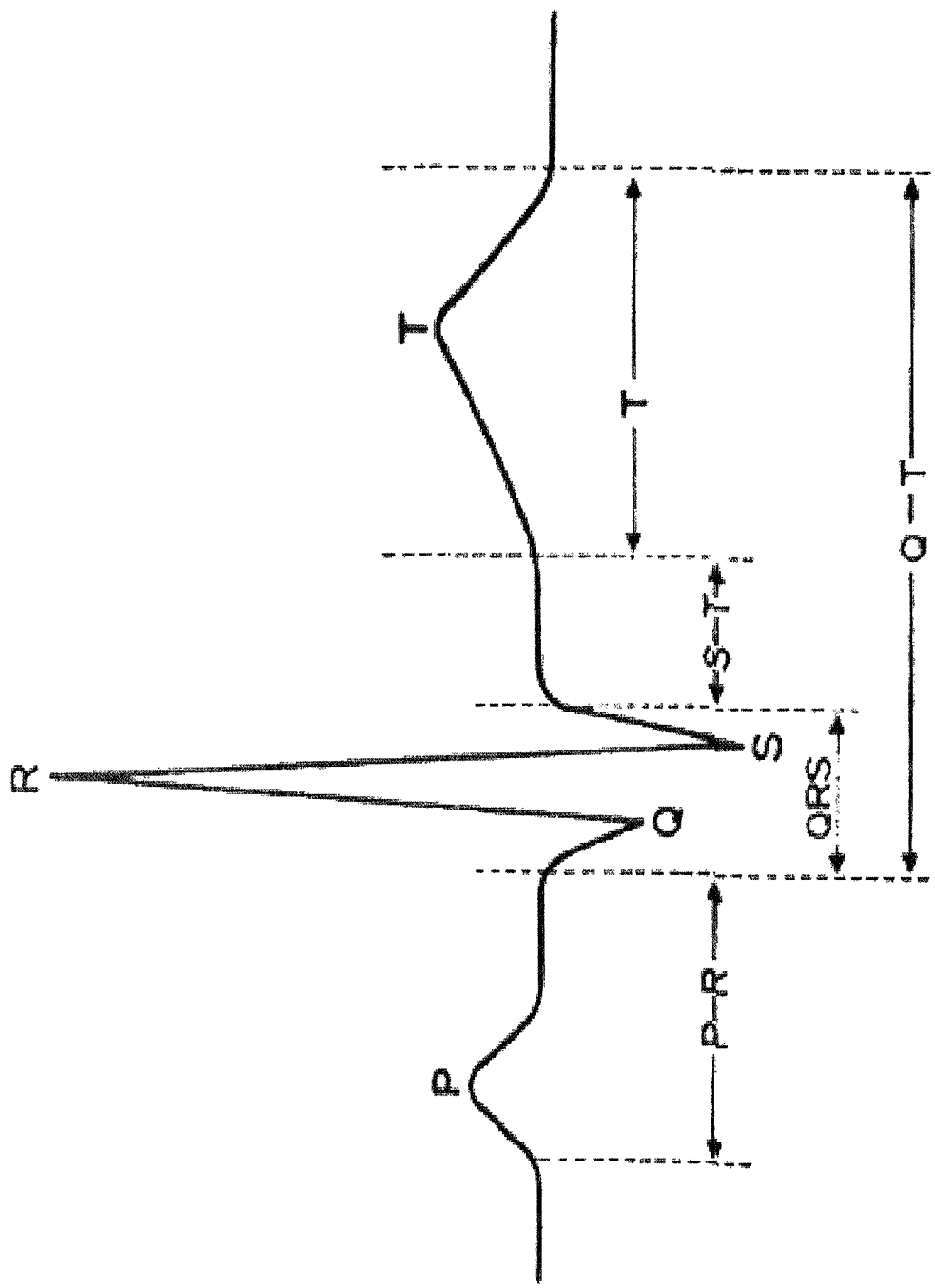
FIG. 2 is an illustration of an ECG tracing that identifies the various peaks of an electrical profile of a normal heartbeat.
Figure 3:
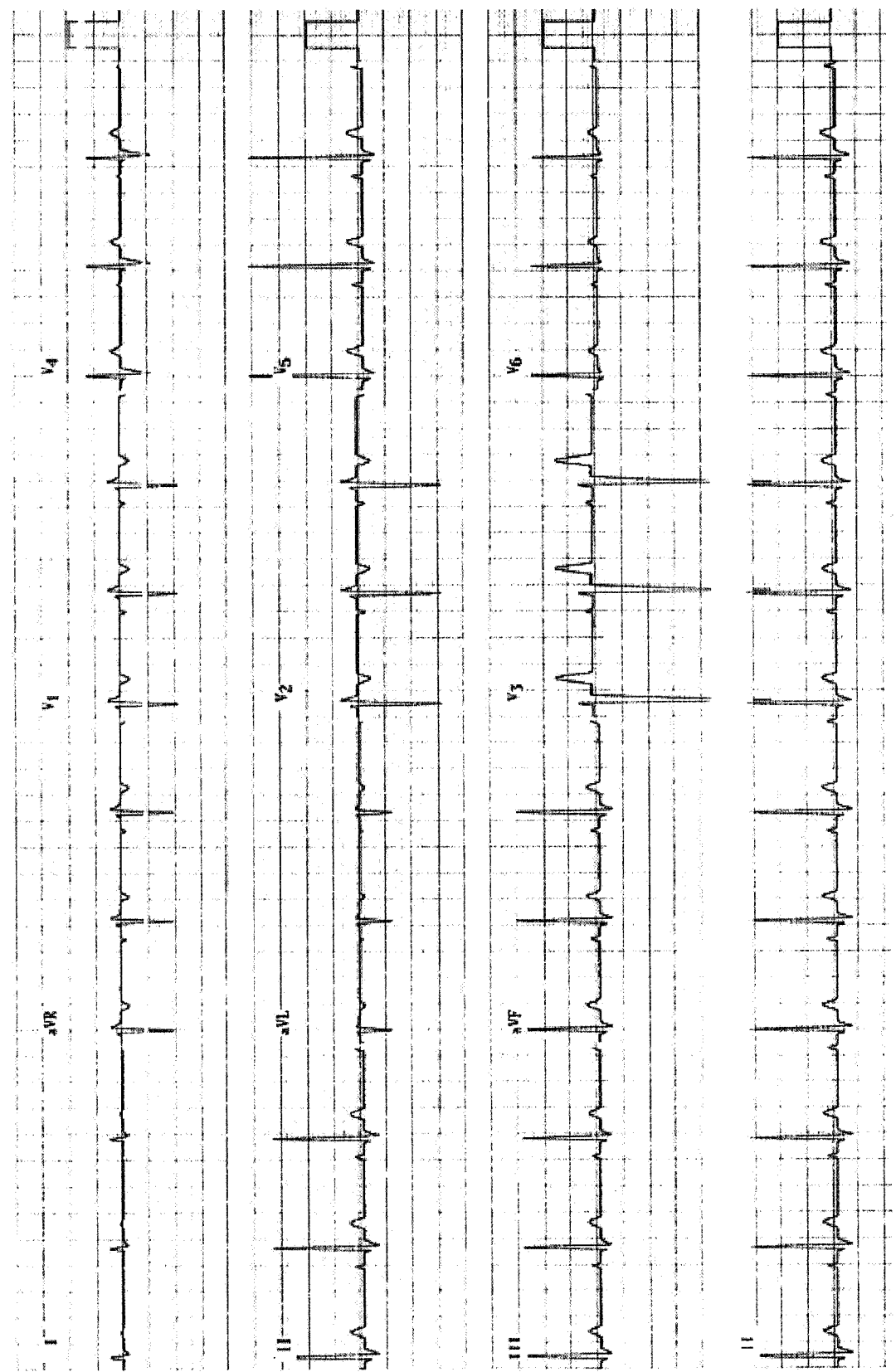
FIG. 3 is an illustration of the output from a 12-lead Holter monitoring device.
Figure 4:
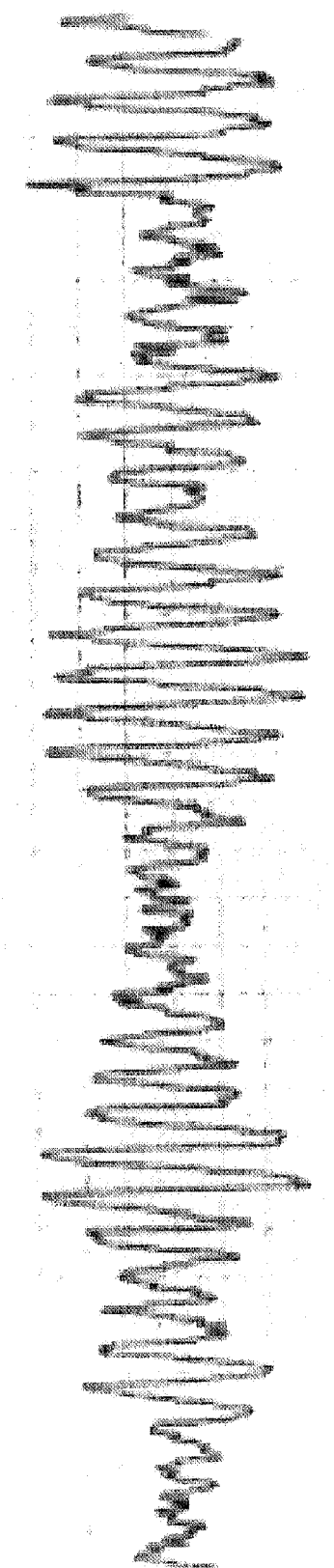
FIG. 4 is an illustration of ECG tracing showing torsades de pointes.

DETAILED DESCRIPTION OF THE ILLUSTRATIVE, NON-LIMITING EMBODIMENTS OF THE INVENTION

Illustrative, non-limiting embodiments of the invention will now be described more fully with reference to the accompanying drawings. A general example of a computer that can be used in accordance with the described embodiment will be described below.

The computer comprises one or more processors or processing units, a system memory and a bus that couples various system components comprising the system memory to the processors. The bus can be one or more of any of several types of bus structures, comprising a memory bus or memory controller, a peripheral bus, an accelerated graphics port and a processor or local bus using any of a variety of bus architectures. The system memory comprises read only memory (ROM) and random access memory. A basic input/output system (BIOS) containing the routines that help to transfer information between elements within the computer, such as during boot up, is stored in the ROM or in a separate memory.

The computer further comprises a hard drive for reading from and writing to one or more hard disks (not shown). Some computers comprise a magnetic disk drive for reading from and writing to a removable magnetic disk and/or an optical disk drive for reading from or writing to a removable optical disk, such as a CD ROM or other optical media. The hard drive, the magnetic disk drive and the optical disk drive are connected to the bus by an appropriate interface. The drives and their associated computer-readable media provide non-volatile storage of computer-readable instructions, data structures, program modules and other data for the computer. Although the exemplary environment described herein employs a hard disk, a removable magnetic disk and a removable optical disk, it should be appreciated by those skilled in the art that other types of computer-readable media which can store data that is accessible by a computer, for example, but not limited to, magnetic cassettes, flash memory cards, digital video disks, random access memories (RAM), read only memories (ROM), etc., may also be used in the exemplary operating environment.

A number of program modules may be stored on the hard disk, magnetic disk, optical disk, ROM or RAM, comprising an operating system, at least one or more application programs, other program modules and program data. In some computers, a user might enter commands and information into the computer through input devices such as a keyboard and a pointing device. Other input devices (not shown) may comprise a microphone, a joystick, a game pad, a satellite dish and/or a scanner. In some instances, however, a computer might not have these types of input devices. These and other input devices are connected to the processing unit through an interface coupled to the bus. In some computers, a monitor or other type of display device might also connected to the bus via an interface, such as a video adapter. Some computers, however, do not have these types of display devices. In addition to the monitor, the computers might comprise other peripheral output devices (not shown) such as speakers and printers.

The computer can, but need not, operate in a networked environment using logical connections to one or more remote terminals. The remote terminal may be, but is not limited to, another personal computer, a server, a router, a network PC, a peer device or other common network node, and typically comprises many or all of the elements described above relative to the computer. The logical connections to the computer may comprise a local area network (LAN) and a wide area network (WAN). Such networking environments are commonplace in offices, enterprise-wide computer networks, intranets, and the Internet.

When used in a LAN networking environment, the computer is connected to the local network through a network interface or adapter. When used in a WAN networking environment, the computer typically comprises a modem or other means for establishing communications over the wide area network, such as the Internet. The modem, which may be internal or external, is connected to the bus via a serial port interface. In a networked environment, program modules depicted relative to the computer, or portions thereof, may be stored in the remote memory storage device. It will be appreciated that the network connections shown are exemplary and other means of establishing a communications link between the computers may be used.

Generally, the data processors of the computer are programmed by means of instructions stored at different times in the various computer-readable storage media of the computer. Programs and operating systems are typically distributed, for example, on floppy disks or CD-ROMs. From there, they are installed or loaded into the secondary memory of the computer. At execution, they are loaded at least partially into the computer's primary electronic memory. The embodiments described herein may comprise these and other various types of computer-readable storage media when such media contain instructions or programs for implementing the steps described below in conjunction with a microprocessor or other data processor. The embodiments also may comprise the computer itself when programmed according to the methods and techniques described below.

Figure 5:
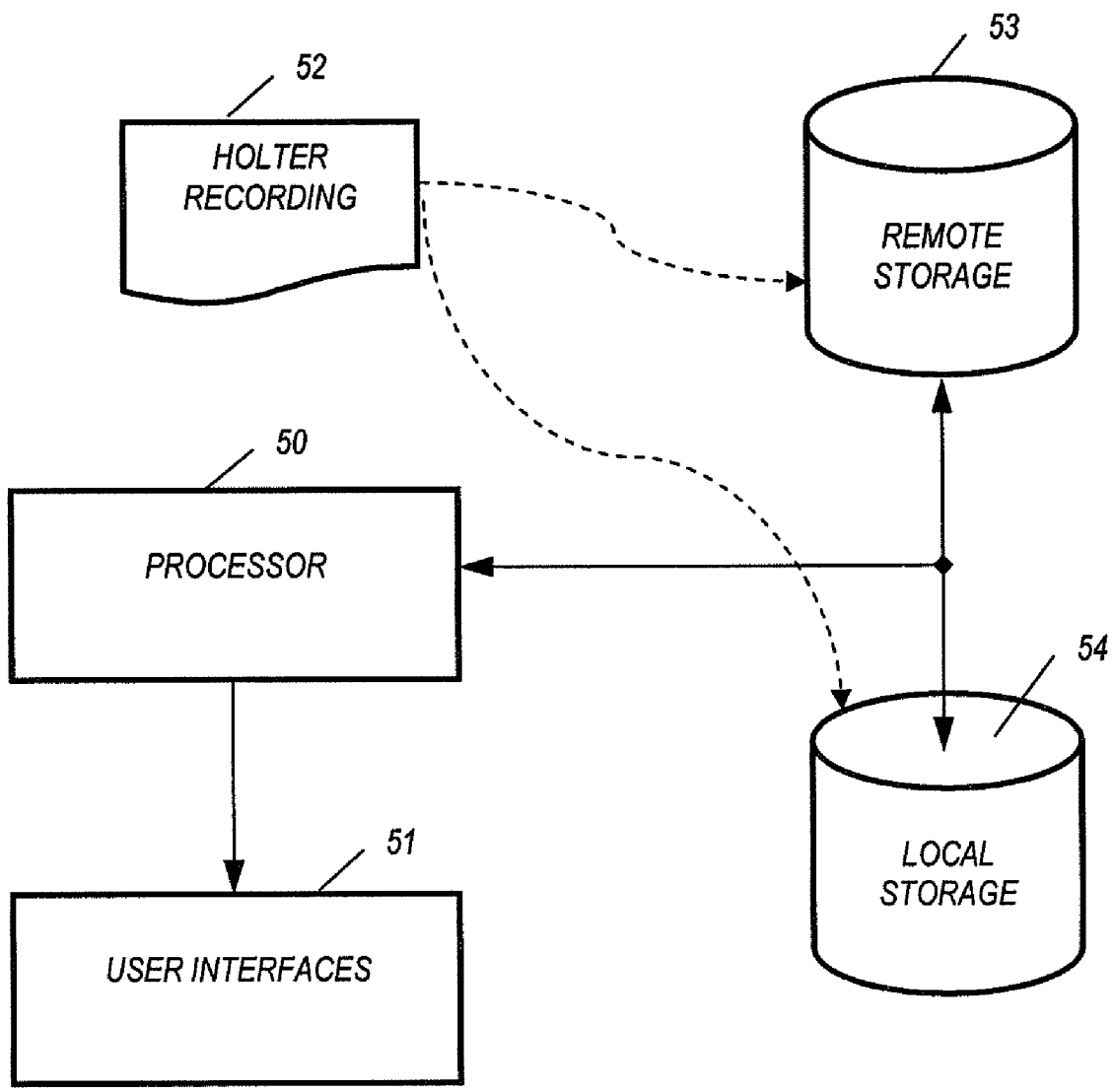
FIG. 5 is an illustration of an exemplary, non-limiting example of a computer system for extracting segments from an electrocardiogram tracing for analysis.

Referring to FIG. 5, an illustrative, non-limiting embodiment of the invention includes a computer that comprises a processor 50, user interfaces 51, and local storage 54. As described above, the processor 50 may comprise one or more processors, and the user interfaces 51 may comprise monitors, keyboards, mice, touch-screens, etc. The processor 50 is connected to the local storage 54 via a bus (or busses) as described above, and the local storage 54 itself may comprise various types of disk memory, electronic memory (i.e., RAM, ROM), or various combinations thereof. The processor 50 may also access the remote storage 53, which itself may comprise various types of data storage machines and/or server machines. The Holter recording file 52, also referred to as an electrocardiogram tracing, is stored in either the remote storage 53 or the local storage 54, and the processor 50 accesses the Holter recording file 52 therefrom.

In one implementation, the computer performs a method for assisting cardiologists in evaluating electrocardiogram (ECG) tracings. The computer acts in a similar fashion to a relatively inexperienced cardiologist who is assisting an expert cardiologist in interpreting captured ECG tracings. Aspects of the embodiment allow the identification of artifacts in the ECG tracing and allow for tentative interpretations of the ECG tracing. Another aspect of the embodiment is the computer's ability to compare several ECG waveforms and group them accordingly, taking into account all presently known information about the waveforms. For instance, if a cardiologist has marked one waveform as normal and another as abnormal, the computer understands that both waveforms cannot be members of the same group, even if they do look similar. In addition, if a cardiologist makes changes to a waveform's interpretation, the computer will regroup the remaining waveforms as needed.

As is known, ECG tracings are stored in a variety of different file formats, such as FDA XML, Mortara XML as exported from E-Scribe, and GE® MUSE®. In one embodiment, the computer may contain conversion libraries to facilitate the conversion of an ECG tracing stored in one of these formats. The conversion libraries allow the computer to process an ECG tracing, without having to worry about the specific format, sample rate, length of recording or other details. Using the conversion libraries, the exemplary embodiments of the present invention operate independently of the data file size, format, sample rate, bit depth and scale factor. Typically, each Holter recording file (i.e., an ECG tracing) will contain 24 or 48 hours of 12-lead data at 1 k samples per second. An exemplary embodiment of the present invention will be able to handle a Holter recording file of at least 48 hours×12 leads×1 k samples per second. Also, embodiments do not have any intrinsic limitations that prevent the handling of longer recordings or recordings taken at higher and/or lower sampling rates.

Although there is no set time limit on the length of an ECG tracing, the typical length of an ECG tracing is about ten seconds. In one implementation, the computer in the present embodiment provides a configurable time limiting function that will truncate ECG tracings that are longer than the configured time limit. Also, the computer may provide a default time limit of ten seconds.

In one embodiment, the computer extracts a number of short segments from a single long ECG tracing, based on settings defined by a study's protocol. The computer may also use an extraction template, which specifies times and amounts of data to extract, relative to drug dosing time. Each protocol has a specific template, which applies across all subjects and all days in the study.

In an exemplary operation, the computer may extract, for example, about six to eighteen ten-second segments that equal approximately two to three minutes out of every thirty to sixty minutes of an ECG tracing. These are typical values, and the extraction template is completely configurable to accommodate drug study protocols. The computer may also choose the ECG tracing segments to extract by checking for the presence of signal artifacts and other defined conditions, and avoid extracting the affected ECG tracing segments. When such conditions in the ECG tracing are detected, the extraction template is adjusted by a limited amount in order to avoid extracting corrupted data from the ECG tracing. For example, ECG traces are usually extracted from a twenty-four-hour Holter recording in triplicate in ten-second time slices. When an artifact or other defined condition is detected, the extraction template is moved to the right or to the left to find ECG traces at the same heart rate within a tolerance of one minute, thereby avoiding the artifact or other defined condition that would otherwise result in the extraction of corrupted data. The net result is that the computer of the present embodiment extracts clean ECG tracing segments that are as close as possible to the desired extraction times. Once the ECG tracing segments are chosen and extracted, the computer automatically exports each individual ECG tracing segment to its own separate file.

The computer may also export the selected ECG tracing segments to a single "sparse" ECG file, i.e., a file that contains multiple non-continuous ECG tracing segments. The sparse file is easier to transmit and store than a group of files, administrative tasks are reduced, and metadata in the file remain unaltered across all of the extracted ECG tracing segments.

In an exemplary embodiment of the present invention, a user (such as a cardiovascular technician) interfaces with a computer system through the computer interfaces described earlier.

Prior to extracting any ECG tracing segments from a Holter recording file, the user may first configure the control settings. In one implementation, the computer system will attempt to fetch and cache the latest control settings from one or more servers that serve as a central repository for control settings. If the server (or servers) is not reachable or accessible for some reason, the computer system may use the last cached control settings.

The control settings comprise a list of various parameters that are set to manage the extraction of the ECG tracing segments. For extraction templates, the control settings change the limits of the extraction template to avoid artifacts in the ECG tracing. For example, the control settings may change the number of seconds to shift the extraction window and the direction in which to shift the extraction window. For annotations to the ECG tracing, the control settings determine the type of annotation channel or channels to create. For example, the control settings can create an artifact channel to be used when scanning the ECG tracing. Alternatively, the control settings can be entered, cached and saved locally for processing Holter recording files. Other types of annotations are possible as well, for example, but not limited to, significant variations in heart rate across ECGs when ECGs are taken in multiple replicates, poor lead attachment and impedance problems. Annotations may also be entered manually using selectable lists, for example, drop-down lists, and free text.

With respect to the extraction of ECG tracings, the control settings can determine what types of data are extracted from the annotations. For example, the control settings might command that only artifact data be extracted from the annotation channel, and all other data in the annotation channel be ignored. The artifact detection settings are set via control settings as well. Artifact detection parameters such as jagged or wandering baseline and thickness of baseline are indicators of artifacts that can be managed via the control settings. Pixel movement can be used to determine jaggedness of baseline. In addition, the control settings can be used to manage the detection of other types of conditions as well, for example, data file output format.

The control settings can also be used to manage the input of ECG tracing files for processing. For example, the control settings can control the operational mode of the file input, such as single file input, batch file input, automatic scanning of directories or integration/control with an automatic workflow control system. The control settings can be used to point to a particular file location, repository, server and/or remote storage system. The control settings can also be used to manage the types of input file formats that are acceptable for processing.

With respect to output of extracted ECG tracing segments, the control settings can be used to set a location, repository, server and/or remote storage system for output files. The control settings can also be used to manage the type of format used for output file generation, and for output file integration/control with an automatic workflow control system.

In an exemplary embodiment of the present invention, updated control settings can be fetched from a central source, which may be a database or other such data storage entity. If a central source for control storage cannot be accessed and/or located, the local copy of the most recent control settings may be used. The active control settings for each ECG analysis are archived for audit trail purposes.

In an exemplary embodiment of the invention, when allowed by a particular output file format, each extracted ECG tracing is tagged with metadata that points back to the control settings used to extract that ECG tracing.

After the control settings have been established, the user next commands the computer system to begin processing Holter recording files to extract the desired ECG tracing segments. The user has several options for commanding the computer system to process the Holter recording files, and these options can be configured via control settings. The simplest option is for the user to enter the filename of the desired Holter recording file on a command line. In one implementation, the computer system processes only the Holter recording file, and no other filenames. If batch processing is commanded by the control settings, the user enters a batch file that lists the filenames of one or more Holter recording files, and the computer system processes these files in serial fashion. Another alternative is for the computer system to receive Holter recording files to process as commanded by an external workflow control system. The computer system would process each Holter recording file as commanded by the external workflow control system, and return the results thereto. Finally, if directory scan is commanded via the control settings, the computer system automatically and repeatedly scans a particular directory and/or directories for new Holter recording files. Once a new Holter recording file has appeared in a targeted directory, the computer system performs the ECG tracing segment extraction on the new Holter recording file.

In an exemplary embodiment of the invention, the dosing time associated with a particular Holter recording file is recorded. Typically, a cardiovascular technician performs this step. The dosing time value is an actual hour/minute time, expressed in the local time. The extraction template is then positioned within the time window of the whole Holter recording file, based on the dosing time.

Once a Holter recording file or files have been selected for processing, the computer system scans the Holter recording file for artifacts and other conditions as specified in the control settings. One or more annotation streams that contain metadata concerning the ECG tracing are added "in parallel" with the existing data in the Holter recording file. If the extraction of the ECG tracing segments must rely on annotations previously generated by the capture of the Holter recording file, the computer system verifies that the necessary annotations exist. If the required annotations are non-existent in the Holter recording file, the computer system rejects the file and the user is notified.

Prior to actually extracting ECG tracing segments from the Holter recording file, the whole ECG tracing is analyzed, and at least one metadata/annotation channel is generated (if required by the control settings) that is specifically intended to help guide the extraction process. This metadata/annotation channel is similar to other types of annotations, such as those indicating patient activity or symptoms. The metadata/annotation channel contains information about the presence or absence of conditions that affect the extraction process. Like other running annotation channels or tracks, this channel describes the ECG tracing waveform on a moment-by-moment basis. Each annotation comprises a start time, an end time and other information, such as a Holter lead number. The annotation channel also comprises a description of the condition seen, in a machine-readable format and optionally comprises an equivalent human readable description. A typical annotation message is as follows: "Artifact present at time point X, for Y seconds, on lead III." This annotation message could be encoded in any appropriate machine or human readable format that can be stored in a file, but the underlying message is independent of the formatting and/or representation.

The scanning and annotation of the ECG tracing is managed via control settings that determine the subject matter to be scanned. The purpose of the scanning is to scan for conditions that have some impact on which ECG tracing segments can or cannot be extracted. Typically, the Holter recording file is scanned for artifacts or other conditions (based on control settings) that would prevent a given time section of the ECG tracing from being extracted. The control settings can also control the scanning to search for other user-defined conditions that might influence extraction of the ECG tracing segments. For example, an annotation track that recorded RR intervals (FIG. 1) could be used to allow and/or disallow extraction based on heart rate. A patient symptoms track could be used to tailor the extraction to only those ECG tracing segments where certain symptoms were present. Multiple annotation tracks could also be examined to decide which ECG tracing segments to extract. Annotation tracks from different types of file formats also can be scanned, as file format converter tools become available.

After the annotation process, the computer system scans the Holter recording file and extracts the desired ECG tracing segments that are specified in the extraction template. The computer system uses the annotation track or tracks to avoid corrupted portions of the Holter recording file and to seek out the portions of the Holter recording file that are requested by the extraction template.

The extraction template specifies what ECG tracing segments should be extracted relative to the timing of the drug dosing of the patient. In addition, information concerning the desired output format and the type and sensitivity of artifact detection may be specified in the template as well. In one implementation, the extraction template applies to all Holter recording files for a given drug test protocol, so that the all ECG tracings in that drug test protocol are subjected to the same extraction template. However, the extraction template may be overridden on a per-subject, per-cohort and/or per-day basis, as necessary. Enabling the extraction template to be overridden allows different settings to be used for each day, each cohort and/or each different subject.

Exemplary embodiments of the present invention may also support a remote mode that extracts important ECG segments from a full Holter recording file, and those extracted segments are transmitted to a cardiologist at a higher priority than the remainder of the Holter recording file. The remote mode does not attempt to detect and/or avoid artifacts in the Holter recording file, and the remote mode expands the extraction template to include the ECG tracing on either side of the specific ECG tracing requested by the extraction template. When the extracted data is received by the cardiologist, the extracted ECG tracing segments are reprocessed to remove the ECG tracing that was not requested by the extraction template, as well as remove any ECG tracing segments affected by artifacts.

When the remote mode is engaged, no artifact detection is performed on the ECG tracing, and the capture parameters of the extraction template are expanded so that ECG tracing on either side of any time segment specified in the extraction template is extracted as well. This expanded "window" is configurable, and might be from one to five minutes on either or both sides of the specified time segment. The widened extraction template compensates for the possibility that noise or artifacts do exist in the extracted ECG tracing segment.

Once the computer system has located one or more ECG tracing segments to extract from the Holter recording file, the ECG tracing segments are extracted, and one output file per extracted ECG tracing segment is generated. Each ECG tracing segment output file is tagged with relevant metadata from the Holter recording file, as well as an identifier that describes the control settings used for the extraction. The inclusion of the control settings is for audit trail purposes. An ECG tracing within a Holter recording file that has been previously marked as unextractable is ignored during the extraction process.

Exemplary embodiments of present invention also export the selected ECG tracing segments to a single "sparse" ECG file, i.e., a file that contains multiple non-continuous ECG tracing segments. The sparse file is easier to transmit and store than a group of files, administrative tasks are reduced, and metadata in the file remains unaltered across all of the extracted ECG tracing segments.

With respect to the annotations, based on the control settings, the computer system may delete from the ECG tracing segment output file whatever annotations it created. If no other application needs the annotations, they just waste space and should be deleted from the ECG tracing segment output file.

As noted above, the computer system can be controlled by an external workflow system. The user of the computer system can configure the control settings such that the computer system signals the external workflow system that a Holter recording file has been processed, and that the results are available. If there were any errors, the computer system sends a message to the external workflow system instead. In this manner, a plurality of Holter recording files can be processed on a computer system during periods of low system use.

Figure 6:
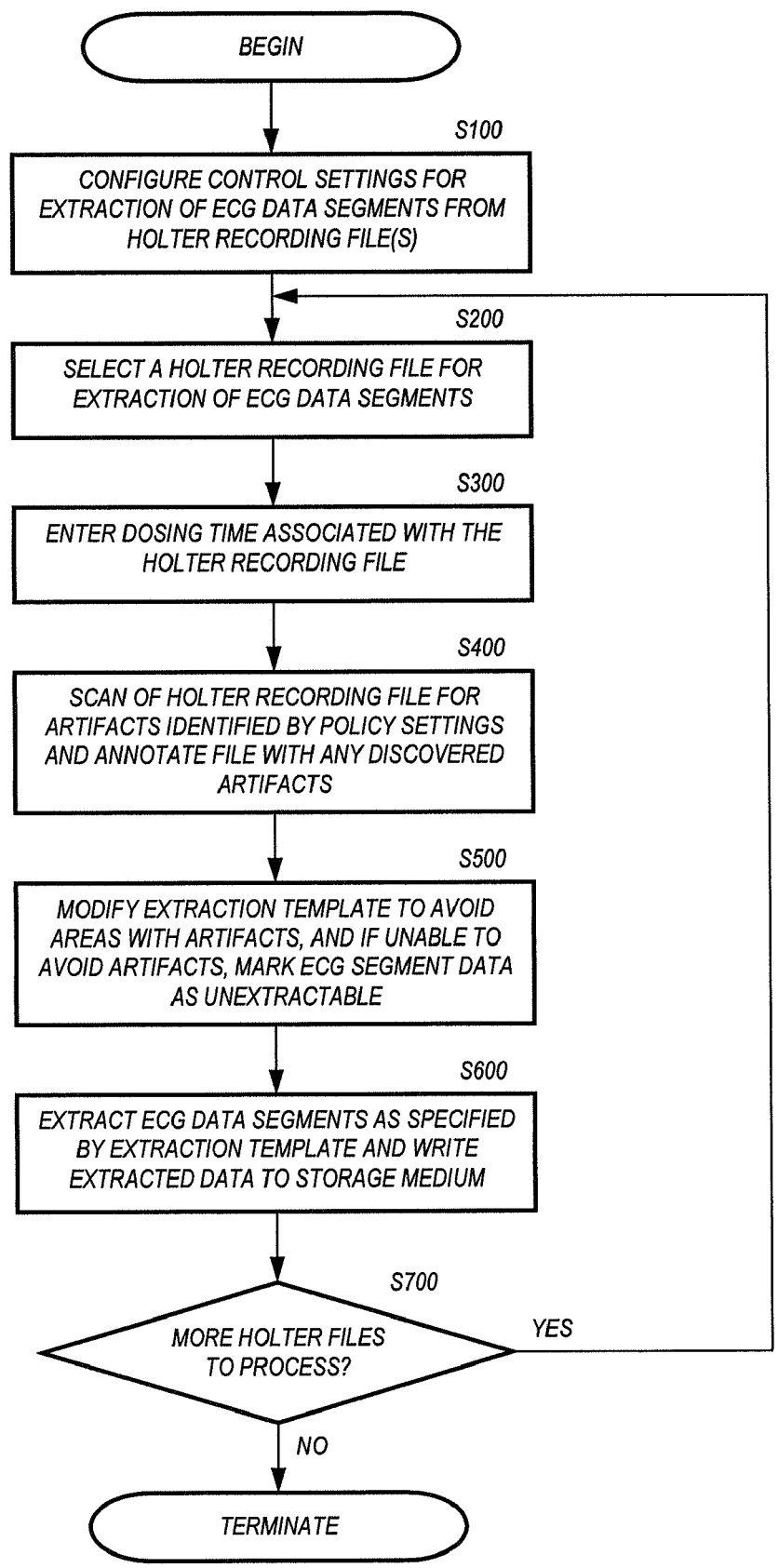
FIG. 6 is a exemplary flowchart illustrating a method for processing electrocardiogram tracings for segment extraction.

FIG. 6 shows a flowchart illustrating a non-limiting method for processing electrocardiogram tracings for segment extraction. At S100, prior to the extraction of ECG tracing segments, the user first configures the control settings. In an exemplary embodiment, the computer system attempts to fetch and cache the latest control settings from one or more servers that serve as a central repository for control settings. If the server or servers are not reachable or accessible for some reason, the computer system uses its last cached control settings. Alternatively, the user can configure the control settings locally at the computer system.

At S200, after the control settings have been established, Holter recording files are selected in order to extract the desired ECG tracing segments. The filename of the desired Holter recording file can be entered on a command line, a batch file that lists the filenames of one or more Holter recording files for batch processing can be entered, Holter recording files for processing can be delivered by an external workflow control system, or directory scan techniques can be used.

Subsequent to the selection of Holter recording files for processing, at S300, a dosing time associated with a particular Holter recording file or files is entered. Typically, a cardiovascular technician performs the entry of the dosing time relative to a Holter recording file or files.

At S400, once a Holter recording file or files have been selected for processing, the Holter recording file is scanned for artifacts and other conditions as specified in the control settings. Prior to actually extracting ECG tracing segments from the Holter recording file, the whole ECG tracing is analyzed, and at least one metadata/annotation channel is generated (if required by the control settings) that is specifically intended to help guide the extraction process. This metadata/annotation channel is similar to other types of annotation, such as those indicating patient activity or symptoms. The metadata/annotation channel contains information about the presence or absence of conditions that affect the extraction process. As discussed with reference to FIG. 9, if the remote mode of extracting ECG tracing segments is engaged, the scanning of a Holter recording file is not performed.

At S500, the extraction template is modified to avoid areas with artifacts. The extraction template is modified at little as possible, and each segment to be extracted within the extraction template is moved to avoid areas with artifacts. If a segment to be extracted is moved past a predetermined threshold, then the region is marked as unextractable. As discussed with reference to FIG. 10B, if the remote mode of extracting ECG tracing segments is engaged, the modification of the extraction template is performed in a different manner.

At S600, one or more ECG tracing segments to be extracted from the Holter recording file are located, the ECG tracing segments are extracted, and one output file per extracted ECG tracing segment is generated. Each ECG tracing segment output file is tagged with relevant metadata from the Holter recording file input file, as well as an identifier that describes the control settings used for the extraction.

At S700, the process determines whether or not any more Holter files need to be processed. If so, the process returns to S200, and if not, the process terminates.

Figure 7:
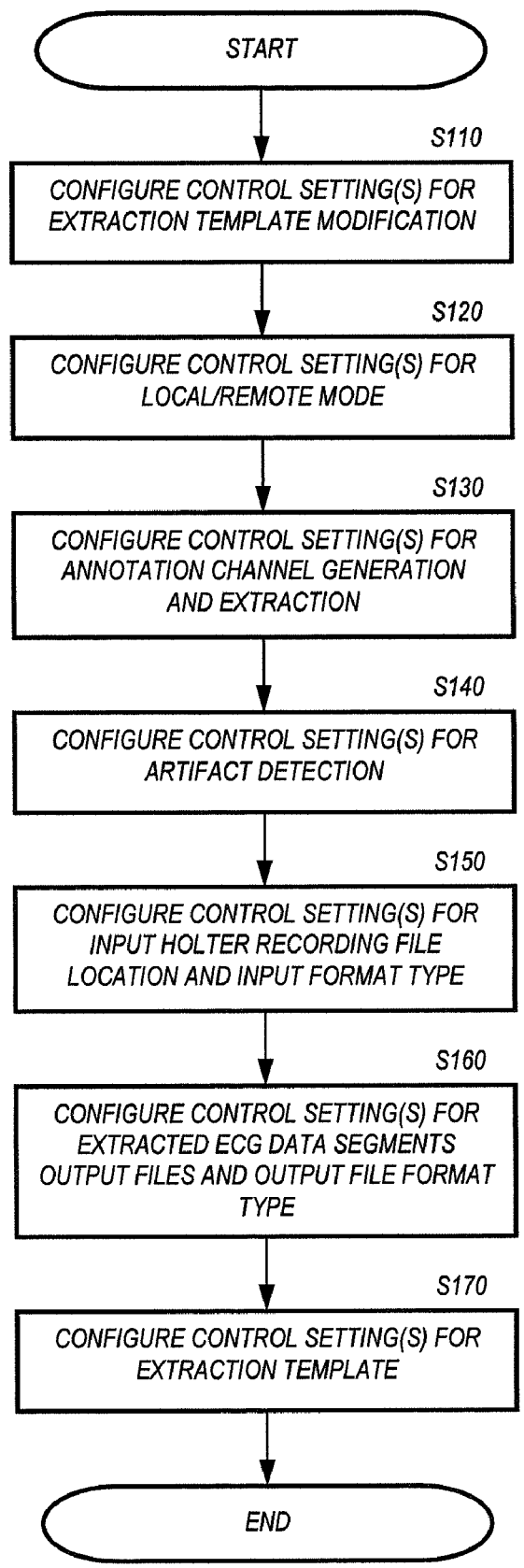
FIG. 7 is an exemplary flowchart illustrating the initialization and/or reconfiguring of control settings for a computer system implementing a method for processing electrocardiogram tracings for segment extraction.

FIG. 7 is a flowchart illustrating a detailed, non-limiting example of the process of S100 in FIG. 6 in which control settings are configured. Although the flowchart in FIG. 7 and other figures illustrate a particular sequence of operations, the sequence of at least some of the operations can be changed by design or modified by a user.

As noted above, the control settings may be retrieved from one or more servers that serve as a central repository for control settings and cached locally. If the server or servers are not reachable or accessible for some reason, the last cached control settings can be used. Alternatively, the control settings can be entered locally for a particular Holter recording file if necessary or for the sake of convenience.

At S110, the control settings for managing changes to the extraction template parameters to avoid identified artifacts in the ECG tracing are entered. For example, a baseline amplitude of less than or equal to seven millivolts (mV) is considered a normal baseline amplitude. The control settings may set a detection amplitude of "n" mV, where "n" is a number greater than seven, to identify a baseline amplitude artifact. Further, a baseline movement tolerance, measured in pixels, may be set.

At S120, the control settings for operating in a remote or local mode are entered. As discussed above, the local/remote setting has an effect on whether a Holter recording file is scanned for artifacts and pre-existing annotations, as well as the manner in which an extraction template may be modified in order to avoid identified artifacts within the Holter recording file.

At S130, the control settings for determining the type of annotation channel or channels to create are entered. The control settings can create an artifact channel to be used when scanning the ECG tracing. Other types of annotations are possible as well, for example, variations in heart rate, poor lead attachment and impedance problems. With respect to the extraction of ECG tracing segments, the control settings can determine what types of data is extracted from the annotations. For example, the control settings might require only artifact data to be extracted from the annotation channel, and all other data in the annotation channel, for example, variations in heart rate and impedance problems, be ignored.

At S140, the control settings for artifact detection settings are entered. For example, artifact detection parameters such as jagged or wandering baseline, and thickness of baseline are entered. In addition, the artifact detection control settings can be used to manage the detection of other types of conditions as well, for example, significant variations in heart rate across ECGs when ECGs are taken in multiple replicates, poor lead attachment and impedance problems.

At S150, the control settings to manage the input of ECH tracing files for processing are entered. The control settings manage the operational mode of the file input, such as single file input, batch file input, automatic scanning of directories or integration/control with an automatic workflow control system. The control settings can point to a particular file location, repository, server and/or remote storage system. In addition, the control settings manage the types of input file formats that are acceptable for processing.

At S160, the control settings for outputting the extracted ECG tracing segments are entered. The control settings set a location, a repository, a server and/or a remote storage system for the output files. The control settings manage the type of format used for output file generation, and for output file integration/control with an automatic workflow control system. When allowed by a particular output file format commanded by the control settings, each extracted ECG tracing is tagged with metadata that points back to the control settings used to extract that ECG tracing.

At S170, the control settings for the extraction template are entered, for example, times and amounts of data to extract relative to drug dosing time.

In an exemplary embodiment of the present invention, updated control information can be fetched from a central source, which may be a database or other such data storage entity. If a central source for control storage cannot be accessed and/or located, the local copy of the most recent control setting is used. The active control settings for each ECG analysis are archived for audit trail purposes.

Figure 8:
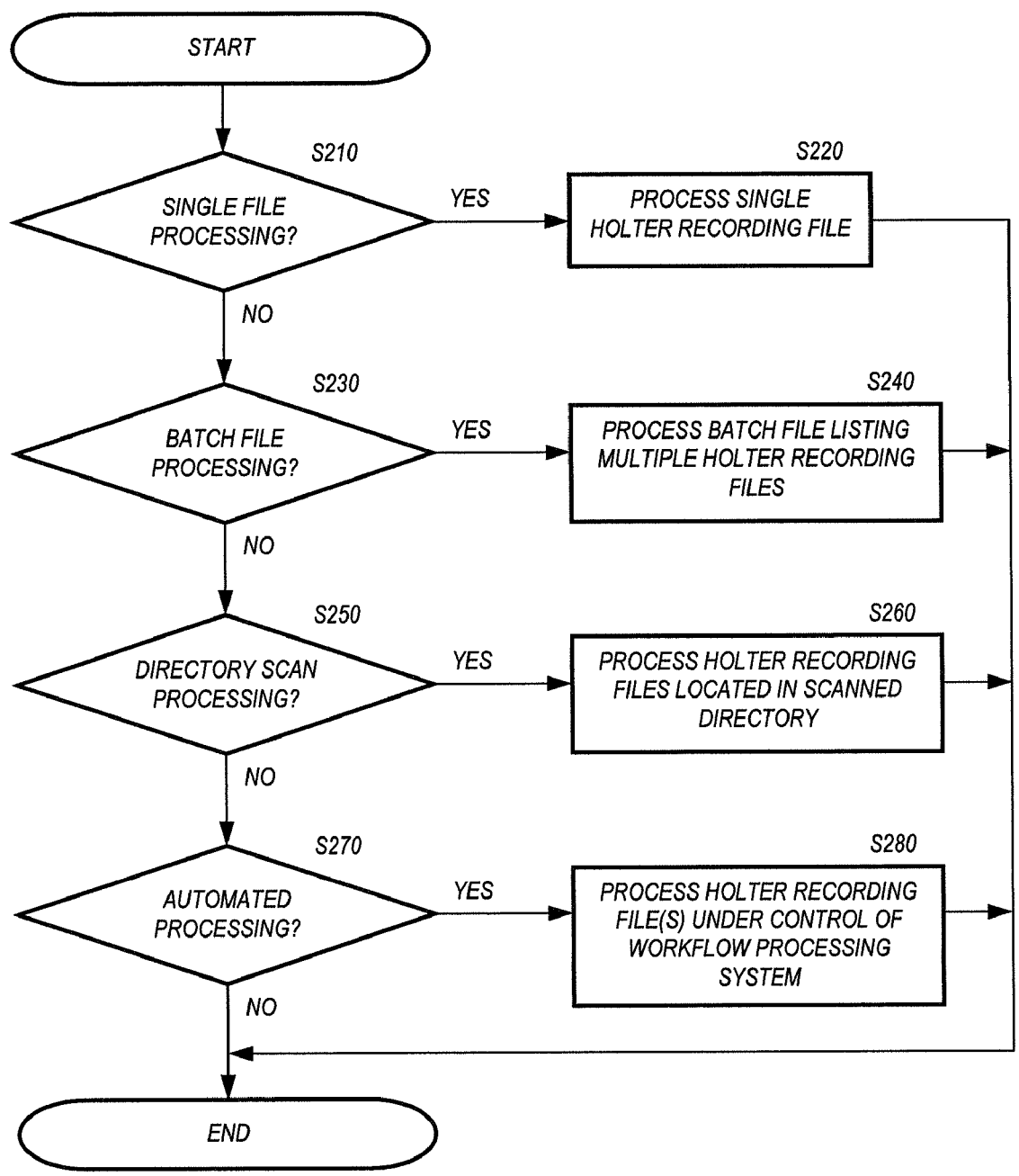
FIG. 8 is an exemplary flowchart illustrating a selection process for segment extraction from electrocardiogram tracings.

FIG. 8 is a flowchart illustrating a detailed, non-limiting example of the process of S200 of FIG. 6 in which Holter recording files are selected.

At S210, if the control setting for processing a single Holter recording file is active, then at S220, the filename of the desired Holter recording filenames is entered, and only that Holter recording filename is processed. Otherwise, at S230, if the control setting for processing a batch of Holter recording files is active, then at S240, a batch file that lists the filenames of one or more Holter recording files is entered, and the listed Holter recording files are processed in serial fashion. Otherwise, at S250, if the control setting for directory scan processing of Holter recording files is active, then at S260, a particular directory or directories are scanned for new Holter recording files. Once a new Holter recording file has appeared in a targeted directory, the ECG tracing segment extraction process is performed on the newly deposited Holter recording file. Otherwise, at S270, if the control setting for automated processing under an external workflow control system is active, then at S280, Holter recording files are processed as commanded by the external workflow control system, and the results are returned thereto.

Figure 9:
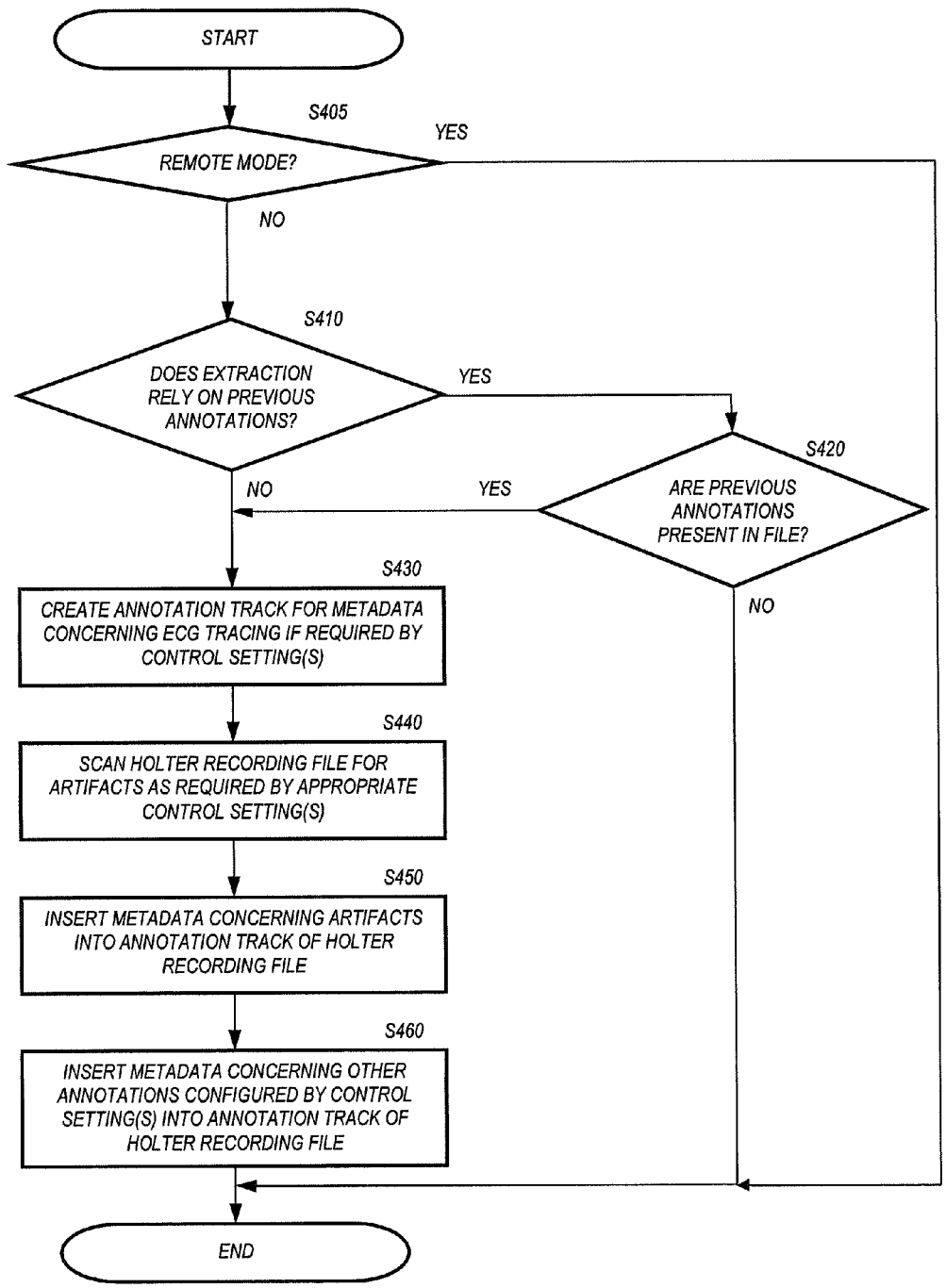
FIG. 9 is an exemplary flowchart illustrating pre-extraction processes of annotation data track creation and scanning of an electrocardiogram tracing for artifacts.

FIG. 9 is a flowchart illustrating a detailed, non-limiting example of the process of S400 of FIG. 6 in which the Holter recording files are scanned for artifacts and annotated.

If the control setting for the remote mode is active (S405: Yes), then the Holter recording file is not scanned for artifacts and is not annotated. Otherwise (S405: No), if the extraction of the ECG tracing segments need to rely on annotations previously generated by the capture of the Holter recording file (S410: Yes), verification of whether the necessary annotations exist takes place at S420. During capture, one or more annotation streams that contain metadata concerning the ECG tracing are added "in parallel" with the existing data in the Holter recording file. If the required annotations are non-existent in the Holter recording file (S420: No), the extraction of ECG tracing segments is not performed.

If the extraction of the ECG tracing segments does not rely on previously generated annotations (S410: No) or such annotations are present in the Holter recording file (S420: Yes), at least one metadata/annotation channel is generated (if required by the control settings) (S430). This metadata/annotation channel is specifically intended to help guide the extraction process and is similar to other types of annotation, such as those indicating patient activity or symptoms. The metadata/annotation channel contains information about the presence or absence of conditions that affect the extraction process. Like other running annotation channels or tracks, this channel describes the ECG tracing waveform on a moment-by-moment basis. Each annotation comprises a start time, an end time and other information, such as a Holter lead number. The annotation channel also comprises a description of the condition seen, in a machine-readable format, and optionally comprising an equivalent human readable description. A typical annotation message is as follows: "Artifact present at time point X, for Y seconds, on lead III." This annotation message could be encoded in any appropriate machine or human readable format that can be stored in a file, but the underlying message is independent of the formatting and/or representation.

At S440, the Holter recording file is scanned for artifacts or other conditions (based on control settings) that would prevent a given time section of the ECG tracing from being extracted. The control settings also control the scanning to search for other user-defined conditions that might influence extraction of the ECG tracing segments. For example, an annotation track that recorded RR intervals could be used to allow and/or disallow extraction based on heart rate. A patient symptoms track could be used to guide extraction to only those ECG tracing segments where certain symptoms were present. Multiple annotation tracks could also be examined to decide which ECG tracing segments to extract.

At S450, metadata concerning any uncovered artifacts in the Holter recording file are inserted into the annotation channel created to assist the extraction of ECG tracing segments.

At S460, metadata concerning other annotations configured by the control settings are inserted into the added annotation track of the Holter recording file.

Figure 10A:
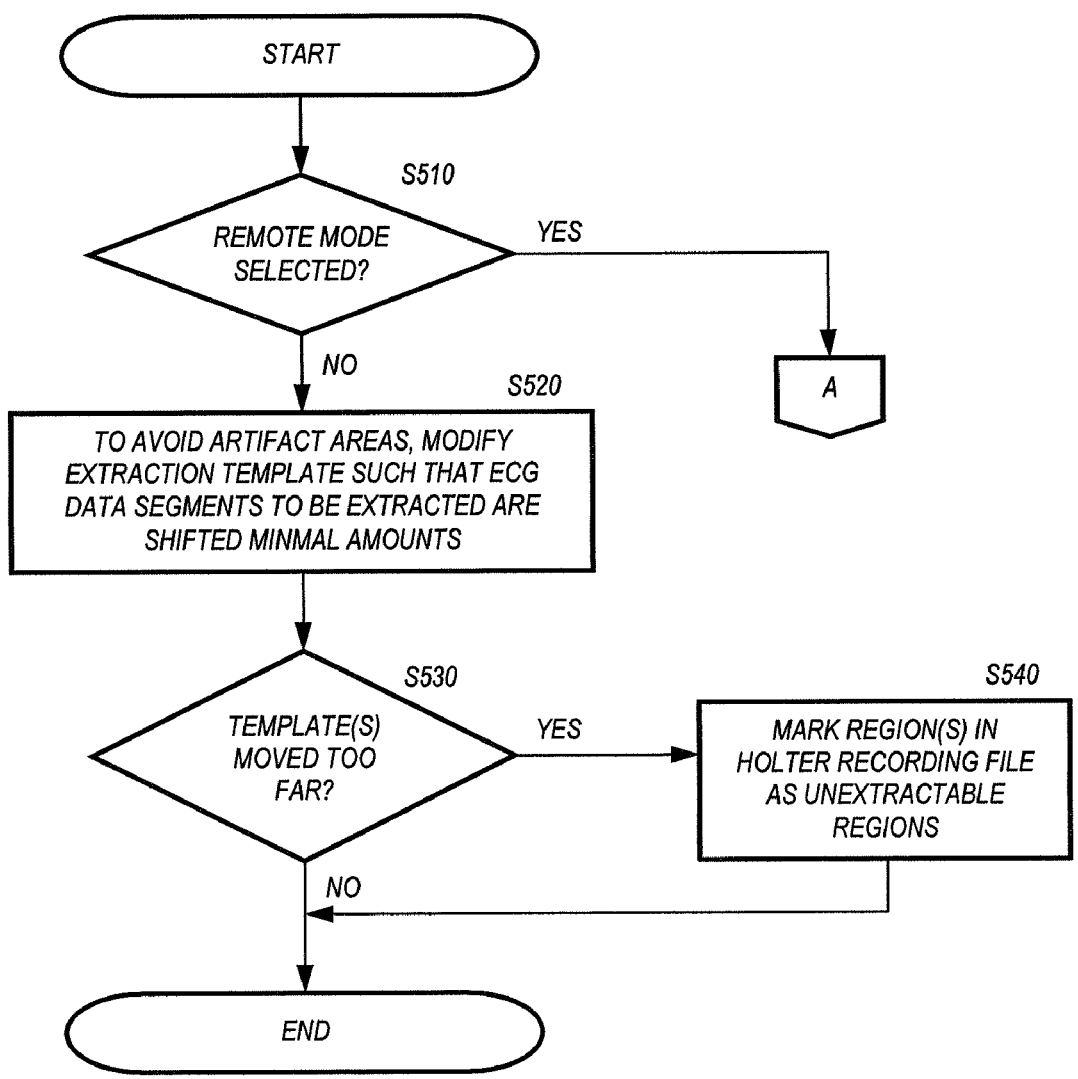
FIG. 10A is an exemplary flowchart illustrating the modification of extraction templates to avoid artifact areas in an electrocardiogram tracing.
Figure 10B:
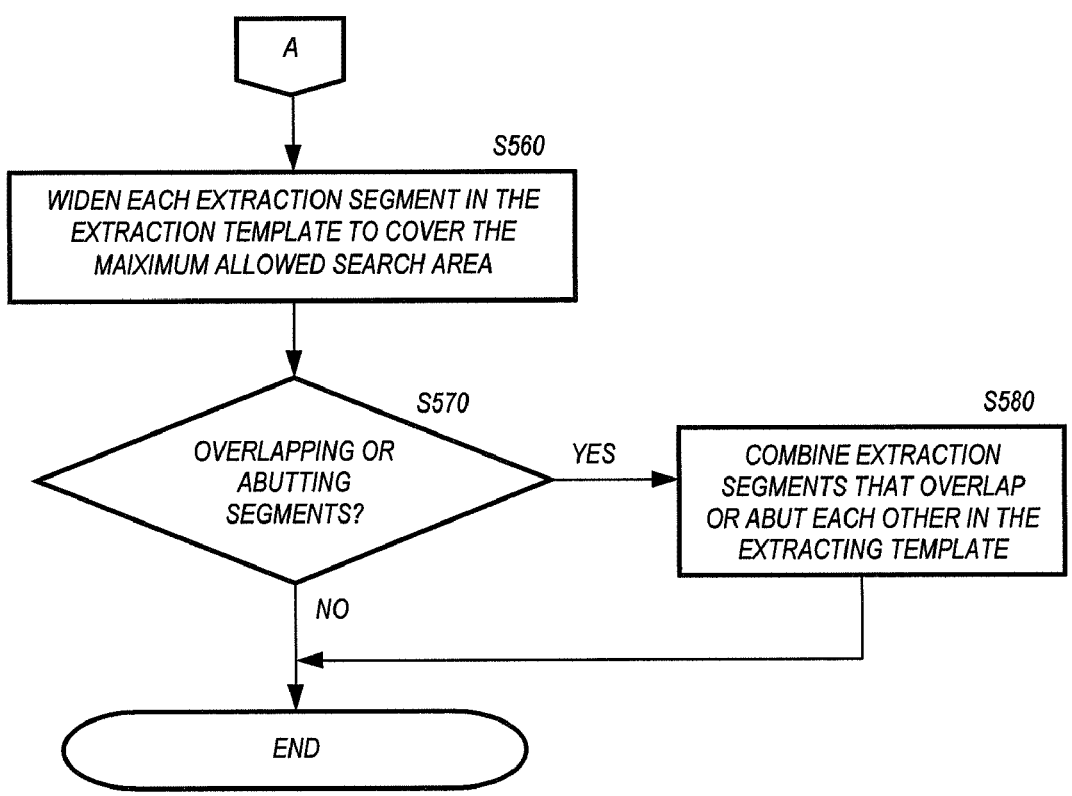
FIG. 10B is an exemplary flowchart illustrating the modification of extraction templates while operating in remote mode.

FIGS. 10A and 10B show a flowchart illustrating a detailed, non-limiting example of the process of S500 of FIG. 6 in which the extraction template is modified.

At S510, if the control setting for remote mode is active (S510: Yes), then a different modification of the extraction template is performed at S560. Otherwise (5510: No), at S520, the extraction template is modified such that ECG tracing segments to be extracted are shifted time-wise to avoid the identified artifact areas. If an artifact is detected, the extraction template is shifted by "n" seconds to the right or to the left from a time point established by the protocol. At S530, a determination is made whether the time-wise shift of the extraction template has exceeded a predetermined threshold. In one embodiment, the extraction window may be shifted by an amount not to exceed 1 minute to extract ECG tracing segments at the same heart rate. If the time-wise shift of the ECG tracing segments to be extracted is too great (S530: Yes), then at S540, those regions in the Holter recording file are marked as unextractable and are ignored during the ECG data segment extraction process.

If remote mode is active (S510: Yes), then at S560, the capture parameters of the extraction template are expanded so that ECG tracing on either side of any time segment specified in the extraction template is extracted as well. This expanded "window" is configurable, and might be from one to five minutes on either side of the specified time segment. The widened extraction template compensates for the possibility that noise or artifacts do exist in the extracted ECG tracing segment. At S570, a determination is made if any of the expanded extraction segments abut one another or overlap one another. If so (S570: Yes), then the abutting/overlapping expanded extraction segments are combined with each other with the extraction template at S580.

The foregoing description of the exemplary embodiments of the invention has been presented for purposes of illustration and description. It is not intended to be exhaustive or to limit the invention to the precise form disclosed, and modifications and variations are possible in light of the above teachings or may be acquired from practice of the invention. The exemplary embodiments were chosen and described in order to explain the principles of the invention and its practical application to enable one skilled in the art to utilize the invention in various exemplary embodiments and with various modifications as are suited to the particular use contemplated.

Thus, while only certain exemplary embodiments of the invention have been specifically described herein, it will be apparent that numerous modifications may be made thereto without departing from the spirit and scope of the invention. Further, acronyms are used merely to enhance the readability of the specification and claims. It should be noted that these acronyms are not intended to lessen the generality of the terms used and they should not be construed to restrict the scope of the claims to the exemplary embodiments described therein.

What is claimed is:

1. A method for extracting segments from an electrocardiogram tracing, the method comprising:
   selecting an electrocardiogram tracing for segment extraction;
   associating a predetermined time with the electrocardiogram tracing to align an extraction template within the electrocardiogram tracing for segment extraction;
   scanning the electrocardiogram tracing for artifacts and annotating the electrocardiogram tracing if any artifacts are discovered;
   if artifacts are present in the segment designated for extraction by the extraction template, modifying the extraction template to avoid the artifacts, and, if unable to modify the extraction template, annotating the electrocardiogram tracing as unextractable; and
   if artifacts are not present in the segment designated for extraction by the extraction template or the extraction template was successfully modified, extracting the designated segment from the electrocardiogram tracing and writing the extracted segment to a storage medium.

2. The method of claim 1 wherein the predetermined time is a dosing time.

3. The method as claimed in claim 1, wherein each extracted segment is written to a separate data file.

4. The method as claimed in claim 1, wherein, prior to the selection of the electrocardiogram tracing, control settings for the extraction of segments are configured.

5. The method as claimed in claim 4, wherein the control settings comprise at least one of an extraction template, an extraction template modification setting, a local/remote setting, an annotation channel generation setting, an artifact detection setting, a type of electrocardiogram tracing file setting and an output file format setting.

6. The method as claimed in claim 1, wherein, after the extracted segment has been written to the storage medium, a determination is made whether additional electrocardiogram tracings are available for extraction.

7. The method as claimed in claim 1, wherein the electrocardiogram tracing is selected for extraction via single file processing, batch file processing, directory scan processing or automated processing.

8. The method as claimed in claim 1, wherein scanning the electrocardiogram tracing for artifacts further comprises:
   determining if the segment extraction depends on annotations being present in the electrocardiogram tracing prior to scanning for artifacts, and if previous annotations are not required, then creating an annotation track for artifact annotations,
   otherwise, if previous annotations are required, then determining if previous annotations are present in the electrocardiogram tracing, and if previous annotations are not present, terminating the processing of the electrocardiogram tracing.

9. The method as claimed in claim 8, wherein, subsequent to the creation of the annotation track, the method further comprises:
   scanning the electrocardiogram tracing for artifacts; and
   if an artifact is detected, inserting data concerning the detected artifact into the annotation track.

10. The method as claimed in claim 9, wherein at least one of the creation of the annotation track, detection of artifacts and insertion of data regarding other annotations are managed by control settings.

11. The method as claimed in claim 1, wherein the modification of the extraction template further comprises:
    shifting the extraction template less than a predetermined amount to avoid extracting a segment containing an artifact therein, and
    if the extraction template shift is greater than a predetermined amount, then inserting data into the annotation track that identifies the desired segment as unextractable.

12. The method as claimed in claim 1, wherein, if commanded by a control setting, the modification of the extraction template further comprises:
    expanding each extraction segment in the extraction template to encompass a predefined maximum extraction size; and
    combining expanded extraction segments that overlap or abut each other.

13. A method for extracting segments from an electrocardiogram tracing, the method comprising:
    selecting an electrocardiogram tracing for segment extraction;
    associating a predetermined time with the electrocardiogram tracing to align an extraction template within the electrocardiogram tracing for segment extraction;
    selecting a remote mode of operation, wherein artifact detection and avoidance is suspended, and the extraction template is widened to include segments of data on either side of extraction times associated with a dosing time;
    extracting the widened segments from the electrocardiogram tracing and writing the extracted segment to a storage medium; and
    transmitting the extracted segments at a high priority to a central database location.

14. The method of claim 13 wherein the predetermined time is a dosing time.

15. A method for using a computer system to extracting segments from an electrocardiogram tracing, the method comprising:
    selecting, via a user interface of the computer system, an electrocardiogram tracing for segment extraction;
    associating, via a user interface of the computer system, a predetermined time with the electrocardiogram tracing to align an extraction template within the electrocardiogram tracing for segment extraction;
    commanding the computer system to scan the electrocardiogram tracing for artifacts and annotating the electrocardiogram tracing if any artifacts are discovered,
    wherein, if artifacts are present in the segment designated for extraction by the extraction template, the computer system modifies the extraction template to avoid the artifacts, and, if the computer system is unable to modify the extraction template, the computer system annotates the electrocardiogram tracing as unextractable; and if artifacts are not present in the segment designated for extraction by the extraction template or the extraction template was successfully modified, the computer system extracts the designated segment from the electrocardiogram tracing and writes the extracted segment to a storage medium.

16. The method of claim 15 wherein the predetermined time is a dosing time.

17. The method as claimed in claim 15, wherein each extracted segment is written to a separate data file.

18. The method as claimed in claim 15, wherein, prior to the selection of the electrocardiogram tracing, control settings for the extraction of segments are configured.

19. The method as claimed in claim 18, wherein the control settings comprise at least one of an extraction template, an extraction template modification setting, a local/remote setting, an annotation channel generation setting, an artifact detection setting, a type of electrocardiogram tracing file setting and an output file format setting.

20. The method as claimed in claim 15, wherein, after the extracted segment has been written to the storage medium, the computer system determines if additional electrocardiogram tracings are available for extraction.

21. The method as claimed in claim 15, wherein scanning the electrocardiogram tracing for artifacts by the computer system further comprises:
determining if the segment extraction depends on annotations being present in the electrocardiogram tracing prior to scanning for artifacts, and if previous annotations are not required, then the computer system creates an annotation track for artifact annotations,
otherwise, if previous annotations are required, then determining if previous annotations are present in the electrocardiogram tracing, and if previous annotations are lacking, the computer system terminates the processing of the electrocardiogram tracing.

22. The method as claimed in claim 21, wherein, subsequent to the creation of the annotation track, the computer system scans the electrocardiogram tracing for artifacts, and if an artifact is detected, inserts data concerning the detected artifact into the annotation track.

23. The method as claimed in claim 22, wherein at least one of the creation of the annotation track, detection of artifacts and insertion of data regarding other annotations are managed by control settings.

24. The method as claimed in claim 15, wherein the computer system modifies the extraction template by:
shifting the extraction template less than a predetermined amount to avoid extracting a segment containing an artifact therein, and
if the extraction template shift is greater than a predetermined amount, then the computer system inserts data into the annotation track that identifies the desired segment as unextractable.

25. The method as claimed in claim 15, wherein, if commanded by a control setting, the computer system further modifies the extraction template by expanding each extraction segment in the extraction template to encompass a predefined maximum extraction size, and combining expanded extraction segments that overlap or abut each other.

26. A method for using a computer system to extracting segments from an electrocardiogram tracing, the method comprising:
selecting, via a user interface of the computer system, an electrocardiogram tracing for segment extraction;
associating, via a user interface of the computer system, a predetermined time with the electrocardiogram tracing to align an extraction template within the electrocardiogram tracing for segment extraction;
selecting, via a user interface of the computer system, a remote mode of operation, wherein artifact detection and avoidance is suspended, and the extraction template is widened to include segments of data on either side of extraction times associated with the dosing time;
extracting the widened segments from the electrocardiogram tracing and writing the extracted segment to a storage medium; and
transmitting the extracted segments at a high priority to a central database location.

27. The method of claim 26 wherein the predetermined time is a dosing time.

28. A computer program product comprising:
a non-transitory computer-readable medium; and
computer executable code embodied on the computer-readable medium that causes a computer to perform predetermined operations, wherein the predetermined operations comprise:
selecting an electrocardiogram tracing for segment extraction;
associating a predetermined time with the electrocardiogram tracing to align an extraction template within the electrocardiogram tracing for segment extraction;
scanning the electrocardiogram tracing for artifacts and annotating the electrocardiogram tracing if any artifacts are discovered;
if artifacts are present in the segment designated for extraction by the extraction template, modifying the extraction template to avoid the artifacts, and, if unable to modify the extraction template, annotating the electrocardiogram tracing as unextractable; and
if artifacts are not present in the segment designated for extraction by the extraction template or the extraction template was successfully modified, extracting the designated segment from the electrocardiogram tracing and writing the extracted segment to a storage medium.

29. The computer program product of claim 28 wherein the predetermined time is a dosing time.

30. A computer program product comprising:
a non-transitory computer-readable medium; and
computer executable code embodied on the computer-readable medium that causes a computer to perform predetermined operations, wherein the predetermined operations comprise:
selecting an electrocardiogram tracing for segment extraction;
associating a predetermined time with the electrocardiogram tracing to align an extraction template within the electrocardiogram tracing for segment extraction;
selecting a remote mode of operation, wherein artifact detection and avoidance is suspended, and the extraction template is widened to include segments of data on either side of extraction times associated with the dosing time;
extracting the widened segments from the electrocardiogram tracing and writing the extracted segment to a storage medium; and
transmitting the extracted segments at a high priority to a central database location.

31. The computer program product of claim 30 wherein the predetermined time is a dosing time.

* * * * *